(12) United States Patent
Al-Zeqri et al.

(10) Patent No.: US 10,017,474 B1
(45) Date of Patent: Jul. 10, 2018

(54) METHOD OF SYNTHESIZING (E)-1,2-DI(PYRIDIN-2-YL) ETHENE-1,2-DIOL

(71) Applicant: KING SAUD UNIVERSITY, Riyadh (SA)

(72) Inventors: Nabil Ahmed Qassim Al-Zeqri, Riyadh (SA); Ismail Khalil Warad, Nablus (PS); Firas Fandi Awwadi, Amman (JO); Ali Mohammed Alsalme, Riyadh (SA); Anas Khaled Abed Alali, Nablus (PS); Abdelkader Zarrouk, Oujda (MA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/860,578

(22) Filed: Jan. 2, 2018

(51) Int. Cl.
*C07D 213/30* (2006.01)

(52) U.S. Cl.
CPC .................. *C07D 213/30* (2013.01)

(58) Field of Classification Search
None
See application file for complete search history.

(56) References Cited

U.S. PATENT DOCUMENTS

| 4,260,757 A | 4/1981 | Wiley |
| 7,897,818 B2 | 3/2011 | Hung |
| 7,989,583 B2 | 8/2011 | Percino Zacarias |

FOREIGN PATENT DOCUMENTS

| JP | H06287287 A | 10/1994 |
| WO | 2016144106 A1 | 9/2016 |
| WO | 2016202875 A1 | 12/2016 |

OTHER PUBLICATIONS

Bark et al, Chemical Communications, vol. 14, pp. 1475-1476. (Year: 1998).*

Hirohama et al., "Copper (II) complexes of 1,10-phenanthroline-derived ligands: studies on DNA binding properties and nuclease activity", Journal of Inorganic Biochemistry, vol. 99, Iss. 5 (2005), pp. 1205-1219 (Abstract only).

Das et al., "Copper Catalysts for Aerobic Oxidation of Alcohols", Chap. 2 in Transition Metal Catalysis in Aerobic Alcohol Oxidation (Cardona et al., ed.), Royal Society of Chemistry (2014), viewable at books.google.com/books?id=nmooDwAAQBAJ&Ipg=PP1&pg=PA40#v=onepage&q&f=false.

Zhang et al., "Copper-catalyzed tandem phosphination-decarboxylation-oxidation of alkynyl acids with H-phosphine oxides: a facile synthesis of Beta-ketophosphine oxides", Chemical Communications (2015), pp. 7839-7842.

Zhang et al., "Novel copper complexes as potential proteasome inhibitors for cancer treatment (Review)", Molecular Medicine Reports, vol. 15, pp. 3-11 (2016) (Abstract only).

Kuckova et al.,Synthesis, Crystal Structure, Spectroscopic Properties and Potential Biological Activities of Salicylate-Neocuproine Ternary Copper(II) Complexes, Molecules (2015), pp. 2115-2137.

* cited by examiner

*Primary Examiner* — Zinna Northington Davis
(74) *Attorney, Agent, or Firm* — Richard C. Litman

(57) ABSTRACT

The method of synthesizing (E)-1,2-di(pyridine-2-yl) ethene-1,2-diol involves dimerization of 2-pyridinecarboxaldehyde (also referred to herein as "picolinaldehyde"). The synthesis of the desired ethene-1,2-diol is achieved using a Cu(II) catalyst to dimerize picolinaldehyde under mild conditions. Preferably, the Cu(II) catalyst is a Cu(II)/neocuproine (2,9-dimethyl-1,10-phenanthroline) complex, or other Cu(II)/phen complex. The reaction in this embodiment may occur at room atmosphere and in ambient light conditions using a water/ROH solvent. The exemplary ethene-1, 2-diol product, (E)-1,2-di(pyridin-2-yl)ethene-1,2-diol has the following structural formula:

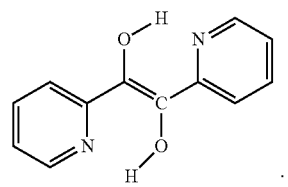

6 Claims, 4 Drawing Sheets

METHOD OF SYNTHESIZING (E)-1,2-DI(PYRIDIN-2-YL) ETHENE-1,2-DIOL

FIELD

The present subject matter relates generally to a diol made by dimerization of an aldehyde, and particularly to a method of synthesizing (E)-1,2-di(pyridine-2-yl)ethene-1,2-diol using a Cu(II) catalyst.

DESCRIPTION OF THE RELATED ART

Copper-based coupling catalysts have relative stability and high reactivity, and exhibit selective light absorption. Since copper is earth-abundant, has known redox properties, and is very cheap, significant promise lies in developing novel complexes involving Cu(I) and Cu(II) ions for potential applications, such as cross-coupling. Developments in copper-based catalysts useful for C—C coupling in both photochemical and electrochemical systems have recently been reported.

Ethene-1,2-diol and its derivatives are important molecules in organic chemistry. Such compounds have been demonstrated in effective pharmaceutical applications, detected in intermediate steps in biological reactions, and used in the synthesis of heterocyclic organic compounds. For such reasons, ethene-1,2-diols and methods of easy and reliably synthesizing such compounds are highly desirable.

Thus, a method of synthesizing (E)-1,2-di(pyridine-2-yl)ethene-1,2-diol solving the aforementioned problems is desired.

SUMMARY

The method of synthesizing (E)-1,2-di(pyridine-2-yl)ethene-1,2-diol involves dimerization of 2-pyridinecarboxaldehyde (also referred to herein as "picolinaldehyde"). The synthesis of the desired ethene-1,2-diol is achieved using a Cu(II) catalyst to dimerize picolinaldehyde under mild conditions. Preferably, the Cu(II) catalyst is a Cu(II)/neocuproine (2,9-dimethyl-1,10-phenanthroline) complex, or other Cu(II)/phen complex. The reaction in this embodiment may occur at room atmosphere and in ambient light conditions using a water/ROH solvent. The exemplary ethene-1,2-diol product, (E)-1,2-di(pyridin-2-yl)ethene-1,2-diol has the following structural formula:

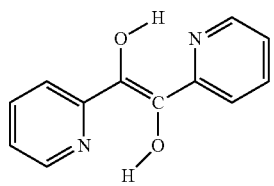

The method of synthesis here can be used to prepare several ene-1,2-diols starting from different types of heterocyclic aromatic aldehyde using similar copper(II) catalysts and system conditions.

These and other features of the present subject matter will become readily apparent upon further review of the following specification and drawings.

BRIEF DESCRIPTION OF THE DRAWINGS

Similar reference characters and acronyms denote corresponding features consistently throughout the attached drawings.

DETAILED DESCRIPTION OF THE PREFERRED EMBODIMENTS

Figure 1:
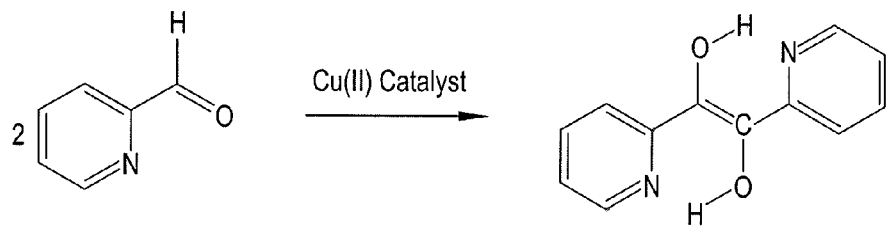
FIG. 1 is a reaction scheme for the method of synthesizing (E)-1,2-di(pyridine-2-yl)ethene-1,2-diol.

The (E)-1,2-di(pyridin-2-yl)ethene-1,2-diol was synthesized starting from Picolinaldehyde, as shown in FIG. 1. In short, Picolinaldehyde was mixed with Cu(II) catalyst, preferably under vigorous stirring, more preferably at 65° C. temperature in open atmosphere and ambient-light using water/ROH solvent. The Picolinaldehyde may be added in excess to the Cu(II) catalyst in solution. The reaction was allowed to continue under the above conditions until the mixture changed color from green to brown. In an exemplary synthesis, the reaction proceeded under the above conditions for 2 hours.

The desired product was confirmed by X-ray single crystal, NMR, MS, FT-IR, EA, TG/DTG, and UV-Vis measurements.

The stability of the hindered desired enediol compound was resonated to show: (1) 3+3+1 total π bonds, conjugated, reflecting several resonance structures formed; (2) the presence of two S6 pseudo intra-hydrogen bonds of type O—H . . . N, and (3) an E-configurational stereoisomer is less sterically hindered compared to the Z-configuration isomer.

Figure 2:
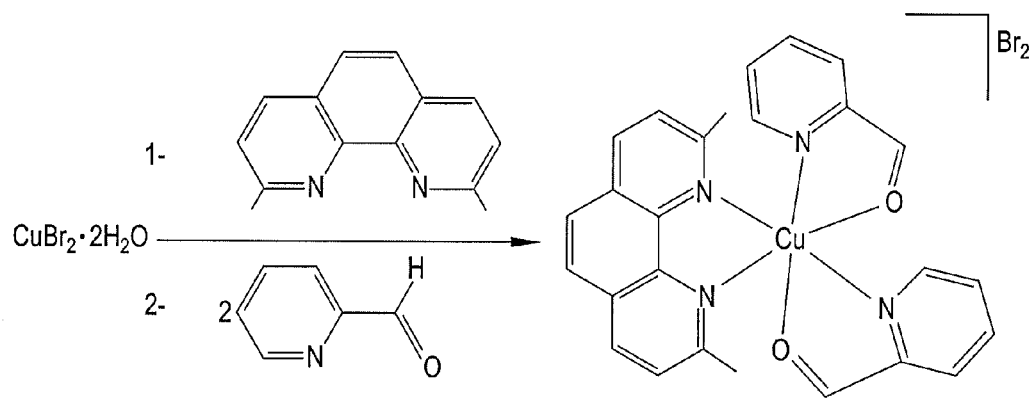
FIG. 2 is a reaction scheme showing details of adding a copper bromide/neocuproine catalyst to 2-pyridinecarboxaldehyde and formation of an intermediate product.

An exemplary Cu(II) catalyst according to an embodiment of the present subject matter is shown in the reaction scheme of FIG. 2. In an experiment, 0.5 g of Picolinaldehyde was added to 0.001 g of Cu(II)Br$_2$/neocuproine complex melted in 20 ml of water/EtOH mixture. This solution was stirred at 65° C. for two hours in open atmosphere/ambient-light conditions. The mixture's color changed from green to brown, indicating the end of the reaction and successful product formation.

Figure 3:
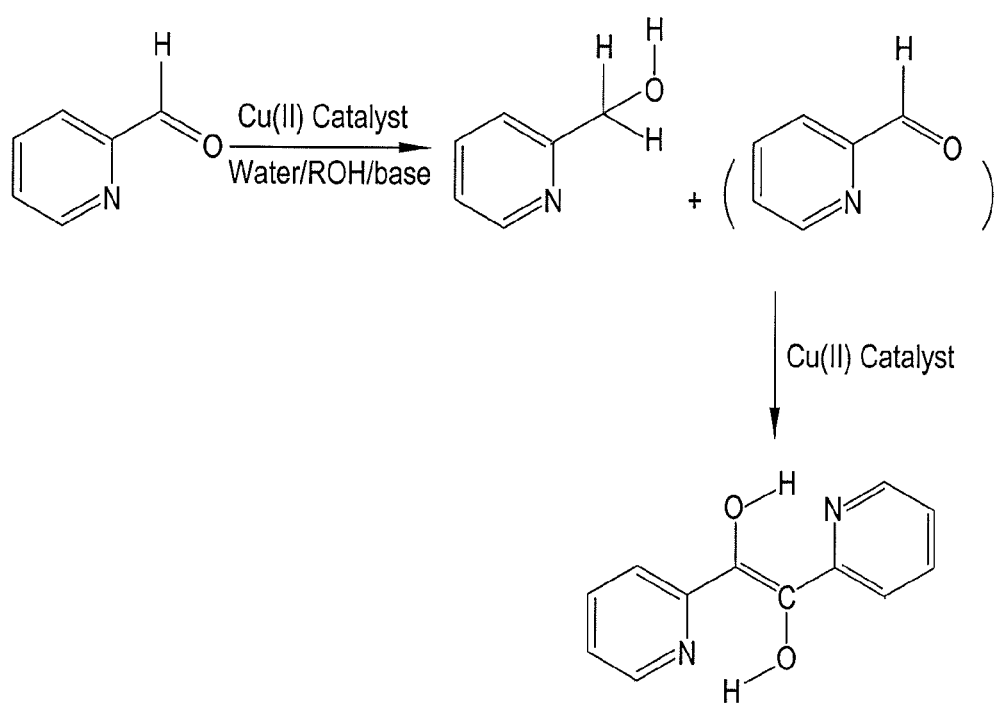
FIG. 3 is a reaction scheme showing a possible reaction mechanism for the method of synthesizing (E)-1,2-di(pyridine-2-yl)ethene-1,2-diol.

From the reaction of 2-pyridinemethanol and 2-pyridinecarboxaldehyde at high temperature and without solvent or catalyst to produce several coupling products including (E)-1,2-di(pyridin-2-yl)ethene-1,2-diol, the reaction mechanism of the exemplary method described herein may be estimated as depicted in FIG. 3.

X-ray crystal diffraction (XRD) studies were performed, including a single crystal structure of the product resulting from the exemplary method above, and a Packing diagram of the product. Tables 1 and 2 show the crystal data and experimental bond lengths and angles of (E)-1,2-di(pyridin-2-yl)ethane 1,2-diol resulting from the exemplary method above. The structure of the expected product is consistent with the XRD solved one; the structure was solved as trans isomer which is reflected in the stability of the desired product. The solved structure reveals two strong intra H-bonds O—H . . . $N_{py}$ with S6 pseudo cyclic units, which stabilize the 3D article structure.

TABLE 1

XRD Data

| | |
|---|---|
| Empirical formula | $C_{12}H_{10}N_2O_2$ |
| Formula weight | 214.22 |
| Temperature | 293(2) K |
| Wavelength | 0.71073 Å |
| Crystal system | Monoclinic |
| Space group | C 1 2/c 1 |
| Unit cell dimensions | a = 16.6045(16) Å  α = 90° |
| | b = 4.6974(5) !  β = 100.082(10)° |
| | c = 13.1661(13) !  γ = 90° |
| Volume | 1011.08(18) !³ |
| Z | 4 |
| Density (calculated) | 1.407 Mg/m³ |
| Absorption coefficient | 0.098 mm⁻¹ |
| F(000) | 448 |
| Crystal size | 0.31 × 0.23 × 0.13 mm³ |
| Theta range for data collection | 3.14 to 26.30° |
| Index ranges | −20 <= h <= 20, |
| | −5 <= k <= 4, −16 <= l <= 16 |
| Reflections collected | 2009 |
| Independent reflections | 1023 [R(int) = 0.0231] |
| Completeness to theta = 26.30 | 99.9% |
| Absorption correction | Semi-empirical from equivalents |
| Max. and min. transmission | 1.00000 and 0.04565 |
| Refinement method | Full-matrix least-squares on $F^2$ |
| Data/restraints/parameters | 1023/0/73 |
| Goodness-of-fit on $F^2$ | 0.985 |
| Final R indices [I > 2 sigma(I)] | R1 = 0.0480, wR2 = 0.1014 |
| R indices (all data) | R1 = 0.0810, wR2 = 0.1159 |
| Largest diff. peak and hole | 0.160 and −0.180 e.!⁻³ |

TABLE 2

XRD Results

| Bond types | A |
|---|---|
| C(3)—C(2) | 1.371(3) |
| C(3)—C(4) | 1.376(3) |
| C(3)—H(3A) | 0.9300 |
| C(4)—C(5) | 1.375(3) |
| C(4)—H(4A) | 0.9300 |
| C(2)—C(1) | 1.397(2) |
| C(2)—H(2A) | 0.9300 |
| C(1)—N(1) | 1.349(2) |
| C(1)—C(6) | 1.460(2) |
| N(1)—C(5) | 1.335(2) |
| C(5)—H(5A) | 0.9300 |
| O(1)—C(6) | 1.3667(18) |
| O(1)—H(1B) | 0.8200 |
| C(6)—C(6)#1 | 1.362(3) |

| Angle types | (°) |
|---|---|
| C(2)—C(3)—C(4) | 119.62(19) |
| C(2)—C(3)—H(3A) | 120.2 |
| C(4)—C(3)—H(3A) | 120.2 |
| C(5)—C(4)—C(3) | 118.31(18) |
| C(5)—C(4)—H(4A) | 120.8 |
| C(3)—C(4)—H(4A) | 120.8 |
| C(3)—C(2)—C(1) | 119.16(17) |
| C(3)—C(2)—H(2A) | 120.4 |
| C(1)—C(2)—H(2A) | 120.4 |
| N(1)—C(1)—C(2) | 121.17(17) |
| N(1)—C(1)—C(6) | 117.33(15) |
| C(2)—C(1)—C(6) | 121.50(16) |
| C(5)—N(1)—C(1) | 118.37(16) |
| N(1)—C(5)—C(4) | 123.36(18) |
| N(1)—C(5)—H(5A) | 118.3 |
| C(4)—C(5)—H(5A) | 118.3 |
| C(6)—O(1)—H(1B) | 109.5 |

TABLE 2-continued

XRD Results

| | |
|---|---|
| C(6)#1—C(6)—O(1) | 122.71(19) |
| C(6)#1—C(6)—C(1) | 123.99(19) |
| O(1)—C(6)—C(1) | 113.30(14) |

Figure 4:
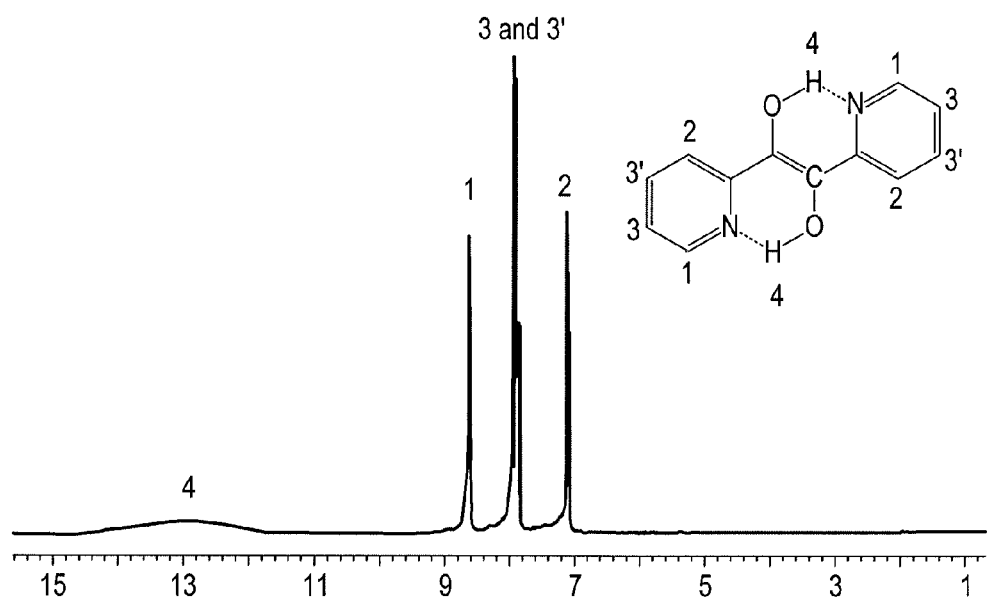
FIG. 4 is the $^1$H NMR spectrum of (E)-1,2-di(pyridin-2-yl)ethene-1,2-diol.

FIG. 4 shows results of ¹H-NMR analysis of the (E)-1, 2-di(pyridin-2-yl)ethene-1,2-diol resulting from the exemplary method above, performed in $CDCl_3$. A typical ¹H NMR reflecting a simple spectrum with high chemical shifts was collected. The pyridine protons were cited as three multiple singles at δ 7.1, 7.9 and 8.7 ppm, and OH protons were detected as a very broad peak at 13 ppm. The chemical shift and the peak broadness of the =C—OH confirmed the presence of intra-hydrogen bonds.

Figure 5:
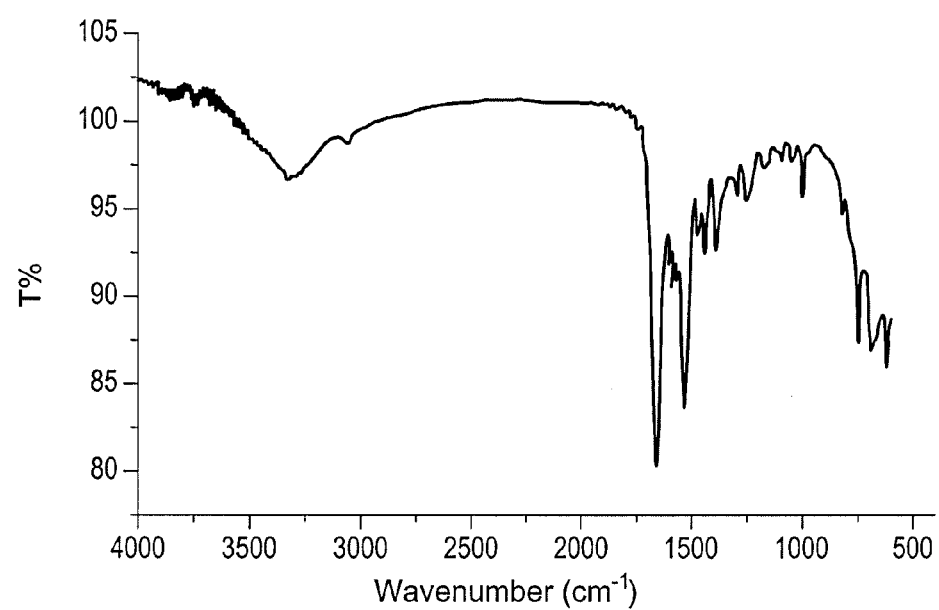
FIG. 5 is the FT-IR spectrum of solid (E)-1,2-di(pyridin-2-yl)ethene-1,2-diol.

FIG. 5 shows the IR-spectrum of the desired ene-1.2-diol product resulting from the exemplary method above, recorded in solid state. The vibration behavior of each functional group appears at the respectively expected positions. The main stretching vibration bands in the spectrum are consistent with the desired compound's structural formula. In particular, these bands include a broad $v_{OH}$ at 3420 cm⁻¹, $v_{(C—H)}$ aromatic at 3080 cm⁻¹, no $v_{(C—H)}$ aliphatic vibration, bending $v_{(OH)}$ at 1630 cm⁻¹ and $v_{(C=N)}$ at 1580 cm⁻¹.

Figure 6:
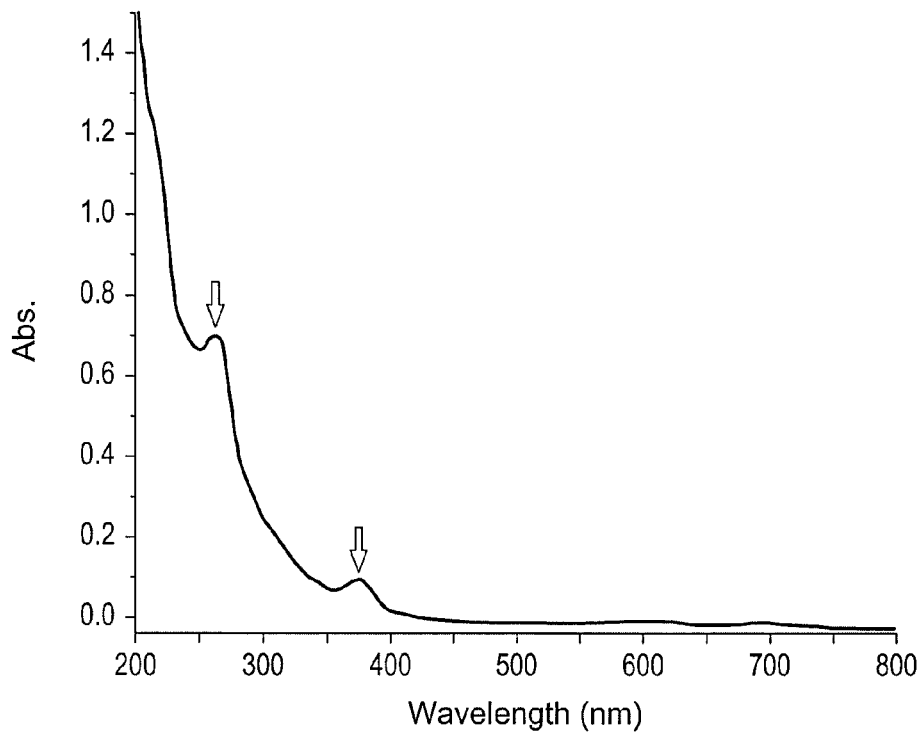
FIG. 6 is the UV-Vis spectrum of $1 \times 10^{-5}$ M of (E)-1,2-di(pyridin-2-yl)ethene-1,2-diol dissolved in MeOH.

FIG. 6 shows UV-Vis absorption behavior of an ethanolic solution of the desired compound, when tested from 200-800 nm. No absorbance was recorded in the visible region. Two sharp singles at $λ_{max}$=270 and 375 nm were recorded in the UV region. These bands are mostly attributed to π-π or n-π electron transfer.

Figure 7:
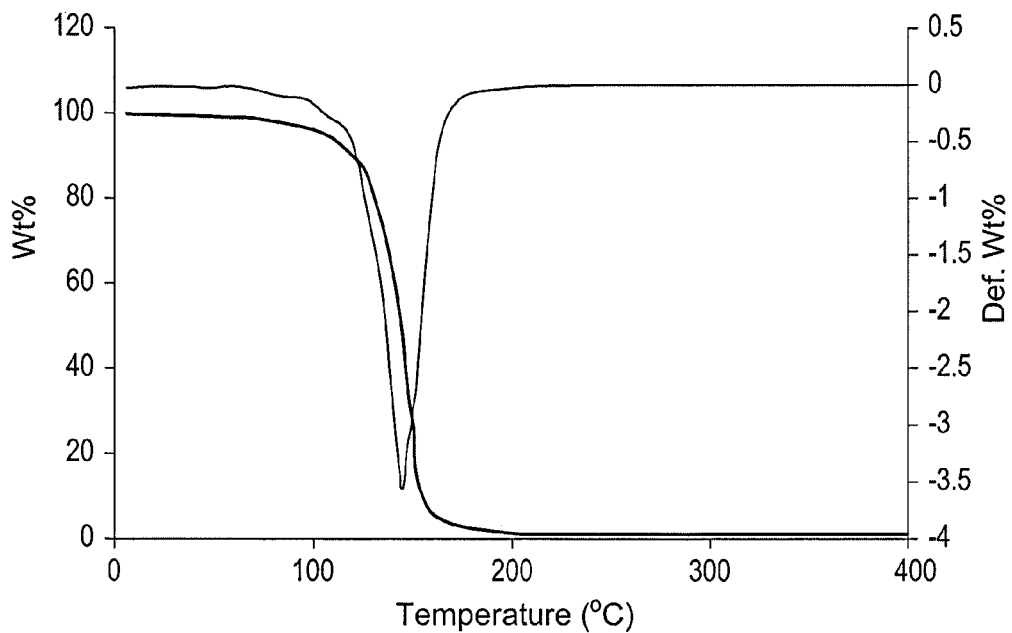
FIG. 7 is a plot showing the thermographic analysis and derivative thermographic analysis TG/DTG curves of (E)-1,2-di(pyridin-2-yl)ethene-1,2-diol.

FIG. 7 shows the results of thermal TG/DTG analyses of the product resulting from the exemplary method above. In particular, FIG. 7 shows good thermal stability of the desired compound in open atmosphere conditions, when measured over a temperature range of 0-400° C. The compound undergoes one-step thermal-decomposition without intermediates. Mostly, the compound was decomposed to light oxide gases, such as $CO_2$, $H_2O$, and $NO_2$.

It is to be understood that the method of synthesizing (E)-1,2-di(pyridine-2-yl)ethene-1,2-diol is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. The method of synthesizing (E)-1,2-di(pyridin-2yl) ethene-1,2-diol comprising the step of adding a CU(II) catalyst to picolinaldehyde in a solvent to form a mixture, wherein the step of forming the mixture occurs under vigorous stirring, and the step of vigorously stirring occurs until the mixture changes color from green to brown.

2. The method of synthesizing (E)-1,2-di(pyridin-2yl) ethene-1,2-diol according to claim 1, wherein the Cu(II) catalyst is a Cu(II)/neocuproine complex.

3. The method of synthesizing (E)-1,2-di(pyridin-2yl) ethene-1,2-diol according to claim 1, wherein the solvent comprises a mixture of water and EtOH.

4. The method of claim 1, wherein the adding step is performed in open atmosphere and ambient-light conditions.

5. The method of synthesizing (E)-1,2-di(pyridin-2yl) ethene-1,2-diol according to claim 1, wherein adding step is performed at a temperature of 65° C.

6. The method of synthesizing (E)-1,2-di(pyridin-2yl) ethene-1,2-diol according to claim 1, wherein the mixture is stirred vigorously for at least 2 hours.

\* \* \* \* \*